United States Patent
Höcker

(10) Patent No.: US 11,747,293 B2
(45) Date of Patent: Sep. 5, 2023

(54) METHOD AND DEVICE FOR DETECTING A NON-CONDENSABLE PORTION OF A MEDIUM WHICH IS AT LEAST IN PART GASEOUS

(71) Applicant: Endress+Hauser Flowtec AG, Reinach (CH)

(72) Inventor: Rainer Höcker, Waldshut (DE)

(73) Assignee: Endress+Hauser Flowtec AG, Reinach (CH)

( * ) Notice: Subject to any disclaimer, the term of this patent is extended or adjusted under 35 U.S.C. 154(b) by 255 days.

(21) Appl. No.: 16/967,354

(22) PCT Filed: Jan. 14, 2019

(86) PCT No.: PCT/EP2019/050808
§ 371 (c)(1),
(2) Date: Aug. 4, 2020

(87) PCT Pub. No.: WO2019/154593
PCT Pub. Date: Aug. 15, 2019

(65) Prior Publication Data
US 2020/0355438 A1    Nov. 12, 2020

(30) Foreign Application Priority Data
Feb. 6, 2018  (DE) .................. 10 2018 102 631.5

(51) Int. Cl.
*G01N 25/02* (2006.01)
*G01N 7/00* (2006.01)
*G01N 11/04* (2006.01)

(52) U.S. Cl.
CPC ............... *G01N 25/02* (2013.01); *G01N 7/00* (2013.01); *G01N 11/04* (2013.01)

(58) Field of Classification Search
CPC .......... G01N 7/00; G01N 11/04; G01N 25/02; F28F 2265/00; F28F 27/00
See application file for complete search history.

(56) References Cited

U.S. PATENT DOCUMENTS

| | | | |
|---|---|---|---|
| 3,234,748 A | 2/1966 | Quick | |
| 3,967,494 A | 7/1976 | Joslyn | |
| (Continued) | | | |

FOREIGN PATENT DOCUMENTS

| | | |
|---|---|---|
| CN | 1151703 A | 6/1997 |
| CN | 1198678 A | 11/1998 |
| (Continued) | | |

OTHER PUBLICATIONS

Human translation of RU2340835C2.*
DIN 8960 : Nov. 1998, Normenausschuß Kältetechnik im DIN Deutsches Institut für Normung, Nov. 1998.

*Primary Examiner* — Nathaniel J Kolb
(74) *Attorney, Agent, or Firm* — Mark A. Logan; Endress+Hauser (USA) Holding, Inc.

(57) ABSTRACT

Disclosed is a method and a device for detecting a non-condensable portion of a medium, which has at least one condensable portion and is present at least partially in gaseous form, wherein in a first method step a temperature measuring device measures a temperature of the medium and a pressure measuring device measures a pressure of the medium, wherein in a second method step a ratio of the pressure to temperature is formed by means of an electronic measuring/operating circuit and this ratio is compared with a desired ratio of a desired pressure and a desired temperature, and wherein in a third method step the electronic measuring/operating circuit outputs a report in case of a minimum deviation of the ratio from the desired ratio.

10 Claims, 3 Drawing Sheets

(56) References Cited

U.S. PATENT DOCUMENTS

Figure 1:
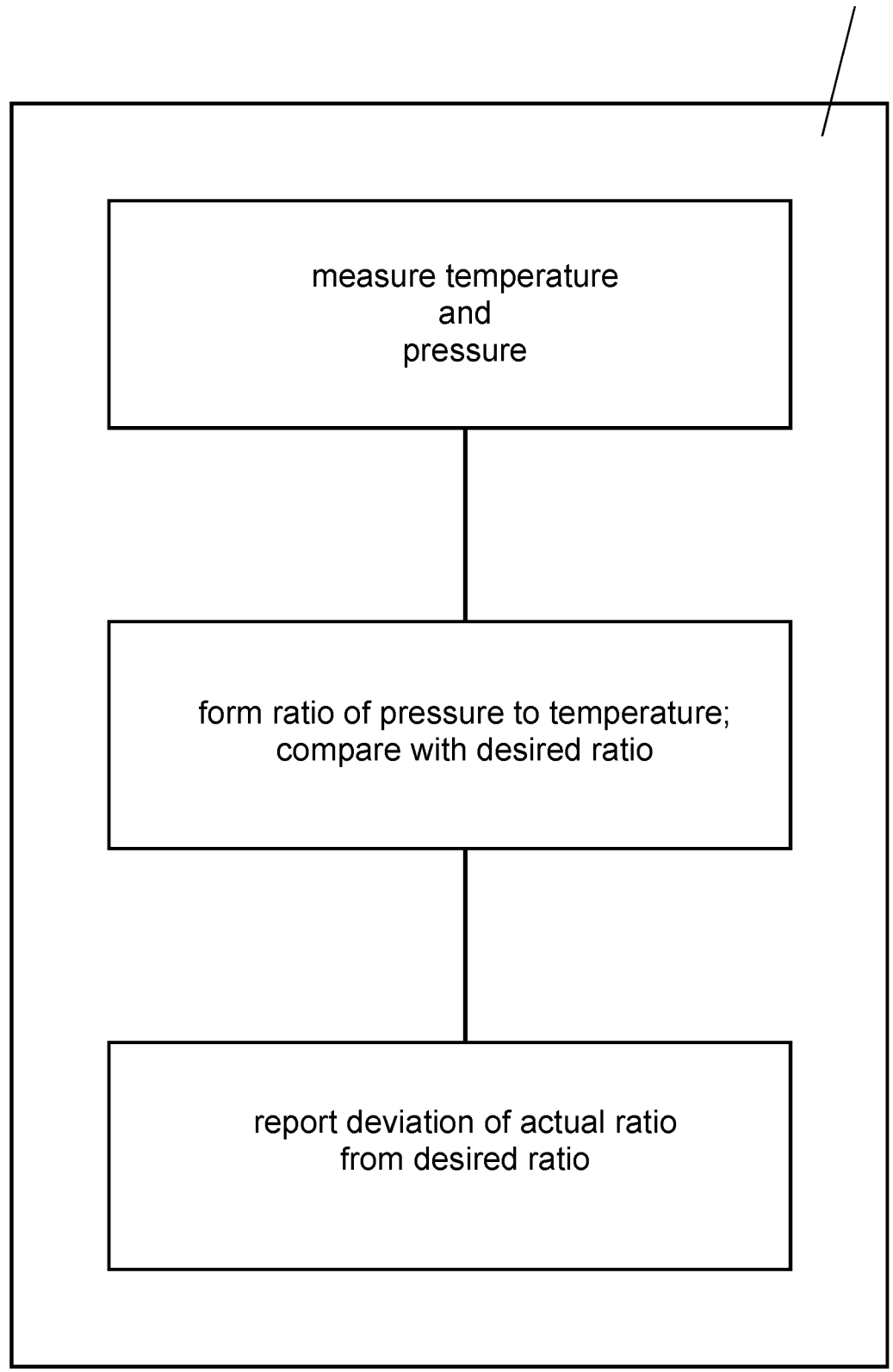

| | | | |
|---|---|---|---|
| 4,739,647 A | | 4/1988 | Monticelli, Jr. |
| 5,752,411 A | * | 5/1998 | Harpster .................... G01F 1/74 |
| | | | 73/861.04 |
| 2003/0071069 A1 | * | 4/2003 | Shelton .................... C02F 1/78 |
| | | | 222/190 |
| 2018/0195889 A1 | * | 7/2018 | Skelding .................... G01F 1/68 |

FOREIGN PATENT DOCUMENTS

| | | | | |
|---|---|---|---|---|
| CN | 1856627 A | | 11/2006 | |
| CN | 203365088 U | | 12/2013 | |
| CN | 109282280 A | | 1/2019 | |
| CZ | 282516 B6 | * | 7/1997 | ............ G21C 17/00 |
| DE | 19718347 A1 | | 11/1998 | |
| EP | 0762902 B1 | | 5/1995 | |
| EP | 1715302 A1 | | 4/2006 | |
| EP | 1882479 A1 | | 7/2007 | |
| EP | 2851679 A1 | | 9/2014 | |
| EP | 3088862 A2 | | 4/2016 | |
| RU | 2340835 C2 | * | 12/2008 | |
| SU | 1746078 A1 | * | 7/1992 | |

\* cited by examiner

METHOD AND DEVICE FOR DETECTING A NON-CONDENSABLE PORTION OF A MEDIUM WHICH IS AT LEAST IN PART GASEOUS

The invention relates to a method and to a device for detecting an undesired non-condensable portion of a medium present in gaseous form.

Gaseous, condensable media, thus, media present in vapor form, are applied technologically for various purposes. Thus, for example, vapor can be utilized to transfer energy to another medium via a heat exchanger. Vapor, especially water vapor, can also be used for sterilization, for example, of medicinal devices, since condensation of water vapor releases large amounts of energy, which reliably kills undesired germs.

In such cases, non-condensable gaseous portions in the vapor, such as, for example, air, are undesirable, since they degrade the functioning of heat exchangers and the sterilization of germs is, in given cases, incomplete.

An object of the invention, consequently, is to provide a method and a device, by means of which a non-condensable portion in a medium present in gaseous form can be zo detected.

The object is achieved by a method as well as by a device as defined in the present disclosure.

In the case of a method of the invention for detecting a non-condensable portion of a medium, which has at least one condensable portion and is present in gaseous form, the method comprises:

measuring in a first method step a temperature of the medium with a temperature measuring device and a pressure of the medium with a pressure measuring device, in a second method step forming by means of an electronic measuring/operating circuit a ratio of the pressure to the temperature and comparing this ratio with a desired ratio, and outputting a report in a third method step by means of the electronic measuring/operating circuit in case of a minimum deviation of the ratio from the desired ratio.

The gaseous medium can, in such case, reside in a container or be flowing through a pipeline. The gaseous medium can carry, or entrain, fine, condensed droplets, thus, be fog-like and can, in such case, be located in a thermodynamic equilibrium, such that it is saturated. Besides a foggy medium, a liquid film or a deposit can form on a wall of the container or pipeline.

Non-condensable means in this connection that the non-condensable portion does not condense in the case of application of the method of the invention. Thus, it is possible, for example, in the case of an air-water vapor mixture, to condense the air portion, if sufficient cooling is performed. However, in the case of a heat exchanger working properly with water vapor, a boiling temperature of a significant air component is never reached. Thus, air in the sense of the invention is non-condensable. The same holds for other methods falling within the scope of the invention.

In an embodiment, the medium is flowing through a pipeline. For example, the pipeline can be part of a thermal power station or a refrigerator. For example, the pipeline is part of a sterilization device.

In an embodiment, a flow measuring device measures a flow of the medium through the pipeline, wherein the electronic measuring/operating circuit ascertains a flow of the condensable portion based on the measured flow as well as the minimum deviation of the ratio, wherein the electronic measuring/operating circuit is associated with the flow measuring device.

In technical devices based on a heat exchange principle, thus, the heat exchange efficiency can be corrected, or ascertained. In the case of sterilization devices, thus, a sterilization efficiency can be given.

In an embodiment, presence of a gaseous medium is verified by means of a verification measuring device, wherein the verification measuring device measures a flow velocity of the medium in the pipeline and/or at least one of the following media properties:

velocity of sound, sound absorption, absorption of electromagnetic radiation, electrical conductivity, density, viscosity, thermal conductivity, amplitude of a surface wave of an inner wall of the container, or the pipeline, frequency of a surface wave of the inner wall of the container, or the pipeline, phase of a surface wave of the inner wall of the container, or the pipeline, wherein in case of a minimum deviation of one of the measured media properties from an expected desired value, or desired value range, the presence of a liquid medium is deduced.

Surface waves of an inner wall of the container or an inner wall of the pipeline are influenced by properties of the medium located in the container, or in the pipeline, and, thus, can be used for verification of presence of a gaseous medium.

The comparison of the ratio of the pressure to temperature with a desired ratio performed in the second method step can also detect a minimum deviation in the case of presence of a liquid medium. In such case, a malfunction or an incorrect interpretation can be prevented by means of a verification.

In an embodiment, the verification measuring device includes a transmitting device and a receiving device for transmitting and receiving acoustic signals or electromagnetic signals.

In an embodiment, the flow measuring device is an ultrasonic, flow measuring device, a thermal, mass flow measuring device, a vortex flow measuring device or a Coriolis flow measuring device.

In an embodiment, the ultrasonic, flow measuring device, or the Coriolis flow measuring device is the verification measuring device.

In an embodiment, the condensable portion of the medium has at a working pressure a boiling point, which is at least 20 K and, especially, at least 40 K and preferably at least 60 K higher than a boiling point of the non-condensable portion.

In an embodiment, the condensable portion includes at least one of the following substances, or at least one substance of at least one of the following substance groups:

water, hydrocarbon, alcohol, ammonia, refrigerant according to DIN-8960 Edition 1998-11.

In an embodiment, the pipeline leads the medium to a heat exchanger, which utilizes a condensation of the condensable portion for heat exchange between the medium and an additional medium.

A device of the invention for detecting a non-condensable portion of a medium, which has at least one condensable portion and is present in the pipeline in gaseous form, wherein the device is adapted for performing a method according to one of the above described versions, comprises:

a temperature measuring device, which is adapted to measure temperature of the medium;

a pressure measuring device, which is adapted to measure pressure of the medium;

a verification measuring device, which is adapted to verify presence of a gaseous state of the medium, an electronic measuring/operating circuit, which is adapted to operate the temperature measuring device, the pressure measuring device as well as the verification measuring device, wherein the electronic measuring/operating circuit is adapted, in case of a minimum deviation of one of the measured media properties from an expected desired value, or desired value range, to deduce the presence of a liquid medium.

In an embodiment, the device includes a flow measuring device, which is arranged downstream or upstream of a pipeline, wherein the flow measuring device has a measuring tube, which is adapted to be connected into the pipeline.

In an embodiment, the verification measuring device is adapted to measure a flow velocity of the medium in the pipeline and/or at least one of the following media properties:

velocity of sound, sound absorption, absorption of electromagnetic radiation, electrical conductivity, density, viscosity, thermal conductivity.

In an embodiment, the flow measuring device is an ultrasonic, flow measuring device, a thermal, mass flow measuring device, a vortex flow measuring device or a Coriolis flow measuring device.

In an embodiment, the flow measuring device is an ultrasonic, flow measuring device or a Coriolis flow measuring device and comprises the verification measuring device.

Figure 2:
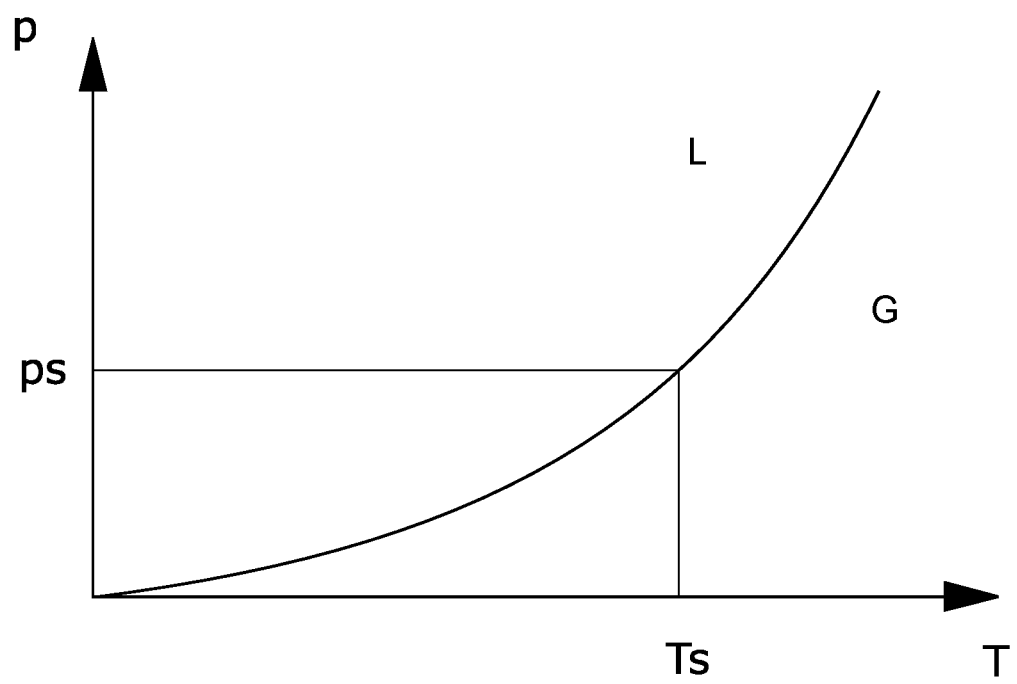
Figure 3:
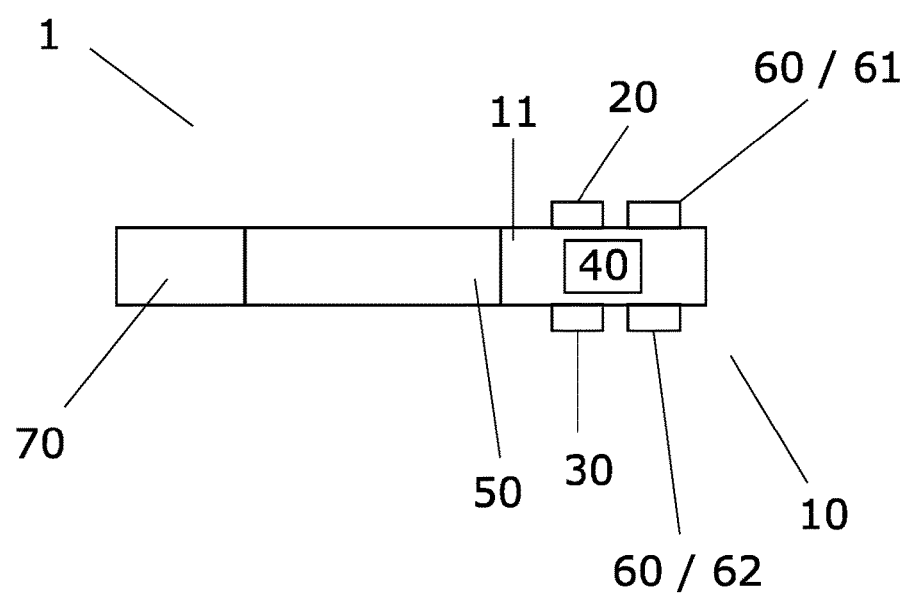

The invention will now be described based on examples of embodiments set forth in the appended drawing, the figures of which show as follows:

FIG. 1 steps of a method of the invention;

FIG. 2 the inventive idea based on a detail from a phase diagram of a condensable portion of an example of a medium; and FIG. 3 by way of example, a device of the invention.

FIG. 1 shows a method 100 of the invention, wherein for detecting a non-condensable portion of a medium in a first method step 101 a temperature measuring device 20 measures a temperature of the medium and a pressure measuring device 30 measures a pressure of the medium. In a second method step 102, an electronic measuring/operating circuit 40 forms a ratio of the measured pressure and the zo measured temperature and compares this ratio with a desired ratio. For a medium, in the case of which a condensable portion is saturated, a saturated vapor pressure curve can be used to determine a desired temperature from a measured pressure, or to determine a desired pressure from a measured temperature, whereupon a desired ratio can be ascertained. A saturated medium present at least partially in gaseous form is often flowing through pipelines, because the medium is introduced into the pipeline as a result of the vapor pressure brought about by boiling a condensed supply of the medium. Since devices used in a plant can have for many reasons an incomplete sealing from the environment, the medium can also have a disturbing, non-condensable portion.

For the case, in which a ratio ascertained from the measured temperature and the measured pressure shows a minimum deviation from the desired ratio, the electronic measuring/operating circuit 40 in a third method step issues a report that the medium is contaminated by a non-condensable portion.

Connected into the pipeline can be a flow measuring device 10, which measures the flow of the medium through the pipeline 50, wherein the electronic measuring/operating circuit ascertains a flow of the condensable portion based on the measured flow as well as the deviation. In this way, for example, the heat transfer efficiency of a heat exchanger connected to the pipeline can be better ascertained.

In order to assure that, for example, no liquid is flowing through the pipeline due to malfunctions, a verification measuring device 60 can be applied, which determines the state of the medium. For example, the verification measuring device can perform a flow measurement or determine media properties, such as, for example, velocity of sound, sound absorption, absorption of electromagnetic radiation, electrical conductivity, density, viscosity, thermal conductivity, amplitude of a surface wave, frequency of a surface wave or phase of a surface wave and based on a certain value of the corresponding media property verify the presence of an at least partially gaseous state. The verification measuring device can have, for example, a transmitting device 61 and a receiving device 62 for transmitting, and receiving, acoustic signals or electromagnetic signals. For example, an ultrasonic, flow measuring device or a Coriolis flow measuring device can undertake the function of verification measuring device.

FIG. 2 shows by way of example a phase diagram of a medium, such as, for example, water or a hydrocarbon or an alcohol or a mixture of at least one of the aforementioned substances, wherein a pressure p and a temperature T of the medium in a saturated state are given by a saturated vapor pressure curve, which shows in a pressure temperature diagram a boundary between a liquid state and a gaseous state.

If at a measurement of the pressure of the medium simultaneously a lower temperature than a desired temperature Ts expected from the saturated vapor pressure curve would be measured, this can be interpreted as indicating presence of a non-condensable portion in the medium. Correspondingly, in case at a measurement of temperature simultaneously a higher pressure than an expected desired pressure ps is present, also this can be interpreted as indicating the presence of a non-condensable portion in the medium. In the case of corresponding interpretation, a volume percentage of the non-condensable portion relative to the total volume can be determined.

FIG. 3 shows by way of example a device 1 comprising a flow measuring device 10, a temperature measuring device 20, a pressure measuring device 30, and a verification measuring device 60, wherein the device 1 is connected with a pipeline 50, which is adapted to lead a medium flowing through the pipeline to a heat exchanger 70. The flow measuring device includes a measuring tube 11, which leads the medium to the pipeline. The temperature measuring device 20 and the pressure measuring device 30 are, in such case, arranged on, or in, the measuring tube. An electronic measuring/operating circuit 40, which is adapted to operate the temperature measuring device, the pressure measuring device, as well as the verification measuring device, is a component of the flow measuring device. Alternatively, the electronic measuring/operating circuit can, however, also be a circuit separated from the flow measuring device. For example, such as here, the verification measuring device 60 can have a transmitting device 61 and a receiving device 62, which serve for transmitting and receiving acoustic signals or electromagnetic signals and which are arranged on, or in, the measuring tube. In the case, in which the flow measuring device is an ultrasonic, flow measuring device, the ultrasonic, flow measuring device can undertake the function of the verification measuring device. Alternatively or supplementally, the transmitting device and the receiving device can also be arranged in a region of the pipeline.

LIST OF REFERENCE CHARACTERS

| | |
|---|---|
| 1 | device |
| 10 | flow measuring device |
| 11 | measuring tube |
| 20 | temperature measuring device |
| 30 | pressure measuring device |
| 40 | electronic measuring/operating circuit |
| 50 | pipeline |
| 60 | verification measuring device |
| 61 | transmitting device |
| 62 | receiving device |
| 70 | heat exchanger |
| ps | desired pressure |
| Ts | desired temperature |
| 100 | method |
| 101 | first method step |
| 102 | second method step |
| 103 | third method step |

The invention claimed is:

1. A method for detecting a non-condensable portion of a medium flowing through a pipeline, wherein the medium includes at least one condensable portion and is present in gaseous form, the method comprising:
   measuring a temperature of the medium with a temperature measuring device and a pressure of the medium with a pressure measuring device;
   forming by means of an electronic measuring and operating circuit a ratio of the pressure to the temperature and comparing the ratio with a desired ratio of a desired pressure and a desired temperature;
   deducing a presence of the non-condensable portion of the medium when the ratio deviates from the desired ratio;
   outputting a report by means of the electronic measuring and operating circuit when the ratio deviates from the desired ratio;
   verifying a presence of a gaseous medium by means of a verification measuring device;
   measuring with the verification measuring device a flow velocity of the medium in the pipeline and at least one of the following media properties: velocity of sound, sound absorption, absorption of electromagnetic radiation, electrical conductivity, density, viscosity, thermal conductivity, amplitude of a surface wave, frequency of a surface wave, and phase of a surface wave; and
   deducing a presence of a liquid medium when one of the measured media properties deviates from an expected desired value or a desired value range.

2. The method as claimed in claim 1 further comprising: ascertaining a flow of the at least one condensable portion based on the measured flow as well as the deviation with the electronic measuring and operating circuit, wherein the electronic measuring and operating circuit is associated with the verification measuring device.

3. The method as claimed in claim 1, wherein the verification measuring device includes a transmitting device and a receiving device for transmitting and receiving acoustic signals or electromagnetic signals.

4. The method as claimed in claim 1, wherein the verification measuring device comprises an ultrasonic flow measuring device a thermal mass flow measuring device a vortex flow measuring device or a Coriolis flow measuring device.

5. The method as claimed in claim 1, wherein the at least one condensable portion of the medium has at a working pressure a boiling point which is at least 20 K higher than a boiling point of the non-condensable portion.

6. The method as claimed in claim 1, wherein the at least one condensable portion includes at least one of the following substances, or at least one substance of one of the following substance groups: water, hydrocarbon, alcohol, ammonia, and refrigerant according to DIN-8960 Edition 1998-11.

7. The method as claimed in claim 1, wherein the pipeline leads the medium to a heat exchanger which utilizes a condensation of the condensable portion for heat exchange between the medium and an additional medium.

8. A device for detecting a non-condensable portion of a medium, wherein the medium includes at least one condensable portion and is present at least partially in gaseous form, the device comprising:
   a temperature measuring device adapted to measure a temperature of the medium;
   a pressure measuring device adapted to measure a pressure of the medium;
   a verification measuring device adapted to verify a presence of a gaseous state of the medium and further adapted to measure a flow velocity of the medium in the pipeline and at least one of the following media properties: velocity of sound, sound absorption, absorption of electromagnetic radiation, electrical conductivity, density, viscosity, thermal conductivity, amplitude of a surface wave of an inner wall of the pipeline, frequency of a surface wave of the inner wall of the pipeline, and phase of a surface wave of the inner wall of the pipeline; and
   an electronic measuring and operating circuit adapted to operate the temperature measuring device, the pressure measuring device, and the verification measuring device, wherein the electronic measuring and operating circuit is further adapted to:
      measure the temperature of the medium with the temperature measuring device and the pressure of the medium with the pressure measuring device;
      form a ratio of the pressure to the temperature and compare the ratio with a desired ratio of a desired pressure and a desired temperature;
      deduce a presence of the non-condensable portion of the medium when the ratio deviates from the desired ratio;
      deduce a presence of a liquid medium when one of the measured media properties deviates from an expected desired value or a desired value range; and
      output a report when the ratio deviates from the desired ratio.

9. The device as claimed in claim 8,
   wherein the verification measuring device is arranged downstream or upstream of a pipeline, and
   wherein the verification measuring device has a measuring tube, which is adapted to be connected into the pipeline.

10. The device as claimed in claim 9, wherein the verification measuring device comprises an ultrasonic flow measuring device a thermal mass flow measuring device a vortex flow measuring device or a Coriolis flow measuring device.

* * * * *